USO10828077B2

(12) United States Patent
Bluchel

(10) Patent No.: US 10,828,077 B2
(45) Date of Patent: Nov. 10, 2020

(54) DISTAL RADIUS WEDGE SCREW

(71) Applicant: Howmedica Osteonics Corp., Mahwah, NJ (US)

(72) Inventor: Tobias Bluchel, Selzach (CH)

(73) Assignee: Howmedica Osteonics Corp., Mahwah, NJ (US)

( * ) Notice: Subject to any disclaimer, the term of this patent is extended or adjusted under 35 U.S.C. 154(b) by 20 days.

(21) Appl. No.: 16/137,903

(22) Filed: Sep. 21, 2018

(65) Prior Publication Data

US 2019/0090922 A1 Mar. 28, 2019

Related U.S. Application Data

(60) Provisional application No. 62/562,042, filed on Sep. 22, 2017.

(51) Int. Cl.
*A61F 2/28* (2006.01)
*A61B 17/80* (2006.01)
*A61B 17/86* (2006.01)
*A61B 17/88* (2006.01)

(52) U.S. Cl.
CPC ........ *A61B 17/8095* (2013.01); *A61B 17/863* (2013.01); *A61B 17/864* (2013.01); *A61F 2/2846* (2013.01); *A61B 17/809* (2013.01); *A61B 17/88* (2013.01)

(58) Field of Classification Search
CPC .................................................. A61B 17/8095
See application file for complete search history.

(56) References Cited

U.S. PATENT DOCUMENTS

| 2,677,369 | A | 5/1954 | Knowles |
| 4,834,757 | A | 5/1989 | Brantigan |
| 5,458,638 | A | 10/1995 | Kuslich et al. |
| 5,609,635 | A | 3/1997 | Michelson |
| 5,776,199 | A | 7/1998 | Michelson |
| 5,800,550 | A | 9/1998 | Sertich |
| 5,860,973 | A | 1/1999 | Michelson |
| 5,865,845 | A | 2/1999 | Thalgott |

(Continued)

FOREIGN PATENT DOCUMENTS

| DE | 4409392 A1 | 9/1995 |
| DE | 29519418 U1 | 5/1996 |

(Continued)

*Primary Examiner* — Zade Coley
(74) *Attorney, Agent, or Firm* — Lerner, David, Littenberg, Krumholz & Mentlik, LLP

(57) ABSTRACT

Provided herein is a wedge for implantation into a distal radius fracture. The wedge has a longitudinal axis and includes a wedge-shaped body and an anchorage reinforcement member having a securement member. The wedge shaped body has opposing tapered surfaces extending from a proximal end wall to a distal end wall and tapering toward the longitudinal axis in the proximal to distal direction. The wedge-shaped body includes an aperture extending through the opposing tapered surfaces. The anchorage reinforcement member is received within the wedge-shaped body and is rotatable relative thereto. At least a portion of the securement member is adapted to extend through the aperture for engaging with and securing to the radius bone.

13 Claims, 5 Drawing Sheets

(56) References Cited

U.S. PATENT DOCUMENTS

| | | | | |
|---|---|---|---|---|
| 6,008,433 A * | 12/1999 | Stone | ..................... | A61B 17/68 623/20.14 |
| 6,129,763 A | 10/2000 | Chauvin et al. | | |
| 6,824,564 B2 * | 11/2004 | Crozet | ................. | A61F 2/4455 623/17.11 |
| 6,855,168 B2 * | 2/2005 | Crozet | ................. | A61B 17/861 623/17.11 |
| 7,335,205 B2 | 2/2008 | Aeschlimann et al. | | |
| 7,537,664 B2 | 5/2009 | O'Neill et al. | | |
| 7,594,932 B2 * | 9/2009 | Aferzon | ................. | A61F 2/447 623/17.16 |
| 8,182,489 B2 | 5/2012 | Horacek | | |
| 8,192,441 B2 | 6/2012 | Collazo | | |
| 8,241,292 B2 | 8/2012 | Collazo | | |
| 8,449,613 B2 * | 5/2013 | Crozet | ................. | A61B 17/861 623/17.11 |
| 8,728,387 B2 | 5/2014 | Jones et al. | | |
| 8,840,666 B2 * | 9/2014 | Crozet | .................... | A61F 2/442 623/17.11 |
| 8,900,310 B2 * | 12/2014 | Carlson | ................... | A61F 2/447 623/17.16 |
| 8,926,618 B2 | 1/2015 | Collazo | | |
| 9,180,010 B2 | 11/2015 | Dong et al. | | |
| 9,226,784 B2 | 1/2016 | Lehmann et al. | | |
| 9,456,901 B2 | 10/2016 | Jones et al. | | |
| 9,456,904 B2 * | 10/2016 | Landry | ................. | A61F 2/4455 |
| 9,463,096 B2 * | 10/2016 | Aferzon | ................. | A61F 2/4611 |
| 9,724,206 B2 | 8/2017 | Aeschlimann et al. | | |
| 10,265,187 B2 * | 4/2019 | Zipnick | ..................... | A61F 2/44 |
| 2002/0038123 A1 * | 3/2002 | Visotsky | ............ | A61B 17/8095 606/304 |
| 2009/0157190 A1 | 6/2009 | Collazo et al. | | |
| 2013/0150969 A1 * | 6/2013 | Zipnick | ................. | A61F 2/4455 623/17.16 |
| 2013/0211522 A1 | 8/2013 | Weiss et al. | | |
| 2014/0135927 A1 * | 5/2014 | Pavlov | .................. | A61F 2/4455 623/17.11 |
| 2017/0189188 A1 * | 7/2017 | Gotfried | ................. | A61F 2/442 |

FOREIGN PATENT DOCUMENTS

| | | |
|---|---|---|
| DE | 29612269 U1 | 9/1996 |
| EP | 0 664 994 A1 | 8/1995 |
| EP | 0 716 840 A2 | 6/1996 |
| EP | 0 732 093 A2 | 9/1996 |
| FR | 2 703 580 A1 | 10/1994 |
| FR | 2 710 519 B1 | 1/1996 |
| FR | 2 724 312 A1 | 3/1996 |
| FR | 2 727 004 A1 | 5/1996 |
| FR | 2 727 003 B1 | 4/1997 |
| WO | 9011740 A1 | 10/1990 |
| WO | 9614809 A1 | 5/1996 |
| WO | 96/27339 A1 | 9/1996 |
| WO | 9640016 A2 | 12/1996 |
| WO | 9715246 A1 | 5/1997 |

* cited by examiner

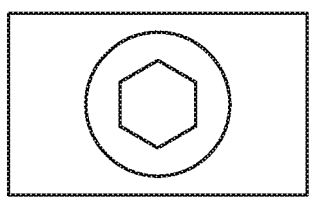
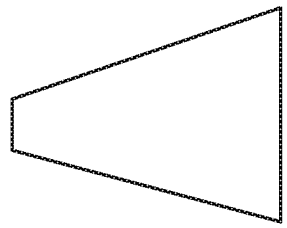
FIG. 7A  FIG. 7B
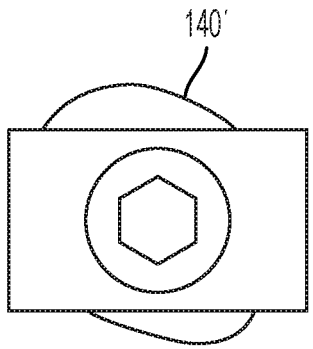
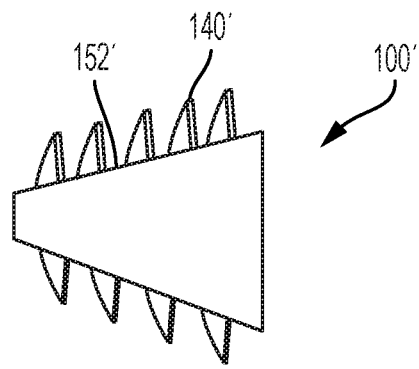
FIG. 7C  FIG. 7D

DISTAL RADIUS WEDGE SCREW

CROSS-REFERENCE TO RELATED APPLICATIONS

The present application claims the benefit of the filing of U.S. Provisional Patent Application No. 62/562,042, filed Sep. 22, 2017, the disclosure of which is incorporated herein by reference.

BACKGROUND OF THE INVENTION

The present invention relates generally to fraction fixation devices and methods for using the same and more particularly to a tapered wedge screw and methods for using the same to maintain reduction of distal radius fractures.

Bone voids or fracture voids may occur in a variety of bones as a result of different injuries or surgical procedures performed to address a deformity. For example, an unstable distal radius fracture is a common injury sustained by a fall on an outstretched hand. This classic fracture is extra-articular or includes a simple intra-articular component, that is, the fracture occurs primarily outside of a joint or may include a simple component within the joint. If not corrected, this type of injury may result in dorsal comminution (i.e. pulverization of the bone in the wrist in the direction of the back of the hand), loss of radial height (i.e., loss of height in the wrist on the side near the thumb), loss of volar tilt (i.e., loss of tilt in the wrist in the direction of the palm of the hand), radial shift (i.e., shift of the wrist towards the side of the thumb), and shortening of the radial column. Poor bone mineral quality and the degree of comminution, may render this type of fracture unstable, such that closed treatment alone may be insufficient. If not reduced, the compression forces experienced by the wrist during routine daily activities can compound the injury and cause the distal radius to fracture across the metaphysis.

Reduction, or architectural restoration, of an unstable fracture may be obtained through a variety of means including plating systems and rigid volar plates. Although plating systems may address cortical reconstitution, they do not address metaphyseal bone voids that are formed when osteopenic/osteoporotic bone collapses. Further, rigid volar plates do not adequately overcome the loss of cancellous bone in the metaphysis when significant comminution and severe loss of bony architecture has already occurred. Additionally, plating systems and rigid volar plate fixation devices are often times more invasive than a patient's bone or fracture void and co-morbidities warrant.

A surgeon-induced void may result from an osteotomy performed on a bone, often a long bone, in connection with addressing a deformity or otherwise in connection with a surgical procedure near a joint, including a joint reconstruction. Examples include a high tibial osteotomy performed on the tibia near the knee joint or an osteotomy performed near the wrist joint. The void would require filling in some fashion, and implants have been used to do so in connection with high tibial osteotomies.

In order to overcome some of the above-mentioned disadvantages, implantable devices have been designed for fixating reduced bone fractures and generally for immobilizing adjacent bone to prevent trauma. For example, U.S. Pat. No. 6,824,564, assigned to applicant, discloses a device for immobilizing adjacent vertebra and is hereby incorporated by reference in its entirety herein as if set forth fully herein. The devices and methods disclosed hereinafter include features that facilitate implantation of the device and maintenance of reduction after implantation.

BRIEF SUMMARY OF THE INVENTION

In accordance with a first aspect of the present invention, a wedge for reduction of a distal radius fracture or filling of a bone void is provided. In one embodiment, the wedge has a longitudinal axis and includes a wedge-shaped body and an anchorage reinforcement member. The wedge-shaped body has opposing tapered surfaces tapering from a proximal end wall to a distal end wall and toward the longitudinal axis in the proximal to distal direction. The wedge-shaped body includes an aperture extending through the opposing tapered surfaces. The anchorage reinforcement member includes a securement member and is at least partially received within the wedge-shaped body. At least a portion of the securement member is adapted to extend through the aperture for engaging with and securing the radius bone.

In accordance with another aspect of the present invention, a method for treating a distal radius fracture or filling a void using a wedge is also provided. The wedge includes a tapered body for placement between opposing bone sections and an anchorage reinforcement member having a securement member attached thereto, whereby at least a portion of the securement member is adapted to extend from the tapered body for engagement with bone. The method includes, in one embodiment, the steps of reducing the distal radius fracture, introducing the distal end of the wedge into the distal radius fracture, and moving the anchorage reinforcement member relative to the wedge-shaped body to drive the wedge into the distal radius fracture. As the wedge moves in the distal direction, the wedge exerts a force on the reduced bone fracture sufficient to maintain reduction of the distal radius together with the tapered body.

BRIEF DESCRIPTION OF THE DRAWINGS

FIG. 7A is a rear view of a wedge according to an embodiment of the invention in an unlocked position.

FIG. 7B is a side view of the wedge of FIG. 7A in the unlocked position.

FIG. 7C is a rear view of the wedge of FIG. 7A in the locked position.

FIG. 7D is a side view of the wedge of FIG. 7A in locked position.

DETAILED DESCRIPTION

As used herein, "axial" means along or parallel to the longitudinal axis of the implant device and "radial" means in the perpendicular direction thereto. "Rotation" refers to rotation about the longitudinal axis unless otherwise described. "Interior" means radially inward, either toward or facing the longitudinal axis, and "exterior" means radially outward or away from the longitudinal axis. The terms "proximal" and "distal", respectively, mean the end of the device nearest the surgeon during a surgical implantation procedure and the opposite end of the device furthest from the surgeon during the surgical implantation procedure.

Throughout this description, a reduced fracture refers to a reduced distal radius fracture, however, the devices and methods described hereinafter can be used to fixate any fracture, naturally occurring or surgeon-induced, such as would be the case in performing a high tibial osteotomy as disclosed in U.S. Pat. Nos. 8,241,292; 8,926,618; 8,192,441; and U.S. Patent Publication No. 2009/0157190, the methods of which are each incorporated by reference in their entirety herein as if set forth fully herein.

Figures 1, 2:
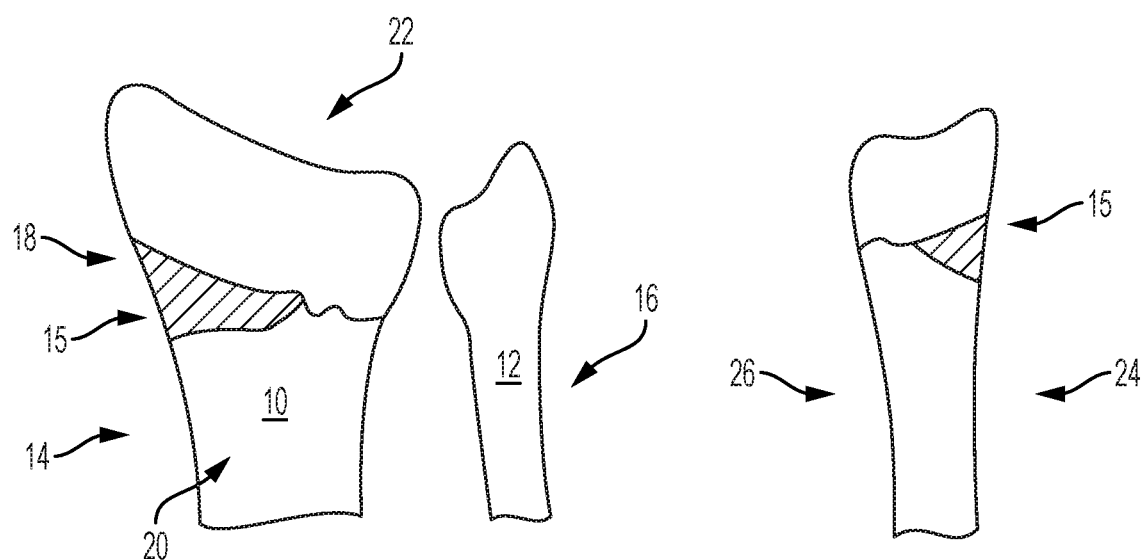
FIG. 1 is a schematic antero-posterior view of a distal radial bone fracture.
FIG. 2 is a schematic side view of a distal radial bone.

FIG. 1 is a schematic anteroposterior view of a wrist, illustrating a distal radius fracture 15 in the radius 10. Also shown is an ulna 12. The distal radial bone fracture 15 is situated on the radial side 14 of the radius 10 opposite the ulnar side 16 and is located in the metaphysis 18 of the radius 10, between the diaphysis 20 and the epiphysis 22. A metaphyseal void (shaded) is present on the radial side 14 of the radius 10. Metaphyseal voids may be surgeon-induced in connection with a surgical procedure or occur as a result of trauma.

FIG. 2 illustrates a schematic side view of the distal radial bone fracture 15, viewed from the radial side of the wrist. FIG. 2 illustrates only the radius 10, as the ulna 12 is substantially hidden behind the radius 10. The radial view depicts that the bone fracture 15 is located predominantly on the dorsal aspect 24 of the radius 10, opposite the volar side 26, and has created a metaphyseal void (shaded) on the dorsal aspect 24 of the radius 10.

The distal radius fracture 15 illustrated in FIGS. 1 and 2 is an exemplary illustration of an unstable, extra-articular fracture, i.e., the fracture is located outside of a joint. This type of fracture 15, if not treated, can lead to many long-term complications including dorsal comminution (i.e., pulverization of the bone on the dorsal side 24 of the radius 10), which may also result in loss of radial height (i.e., loss of height of the bone on the radial side 14 of the radius 10). In addition, the fracture 15 may result in loss of volar tilt (i.e., loss of tilt of the bone towards the volar side 26 of the radius 10). Further, the fracture 15 may result in a radial shift (i.e., shift of the bone towards the radial side 14 of the radius 10) or a shortening of the radial column.

Figure 3:
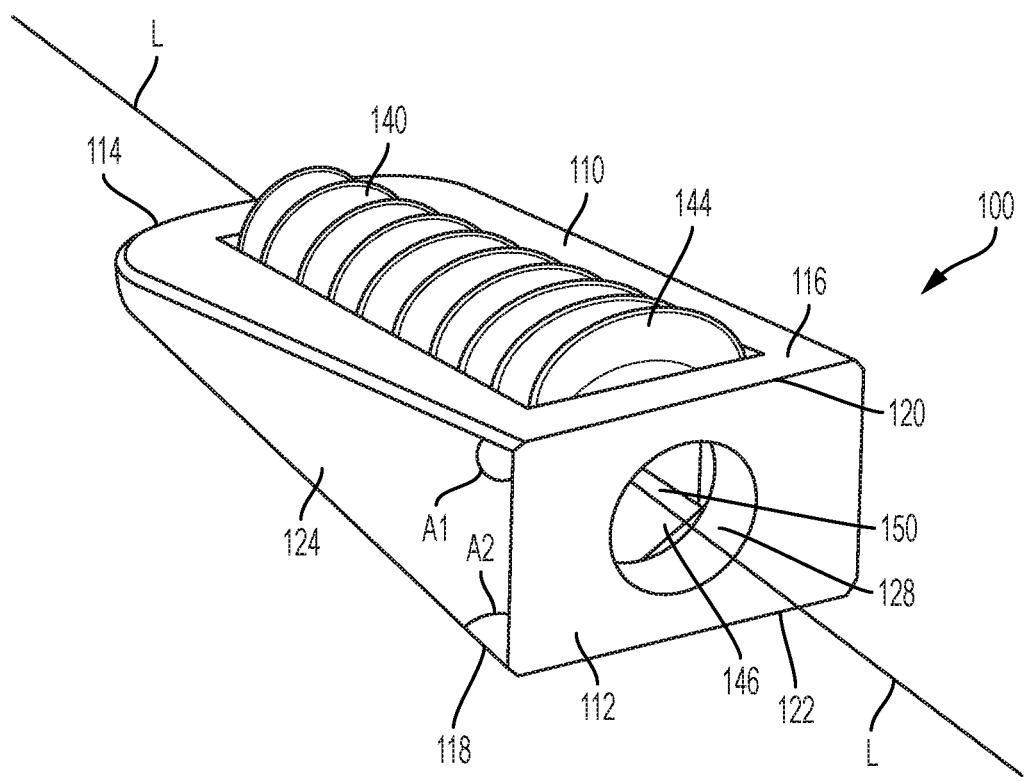
FIG. 3 is an isometric view of a wedge according to an embodiment of the invention.
Figure 4:
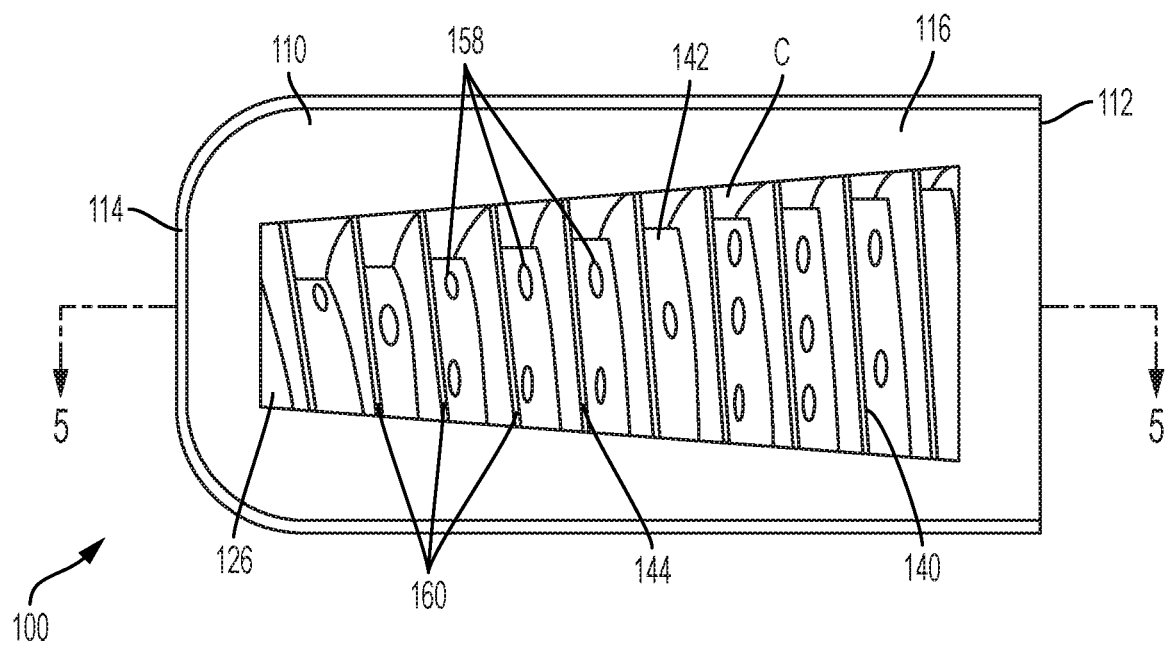
FIG. 4 is a top view of the wedge of FIG. 3.
Figure 5:
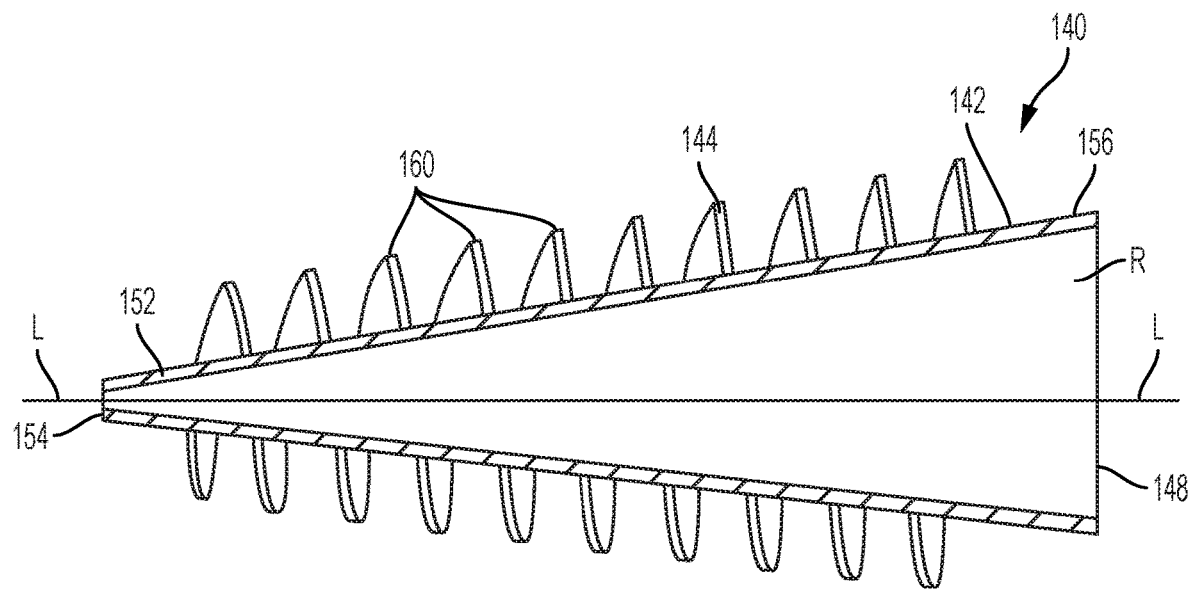
FIG. 5 is a cross-sectional view of the wedge of FIG. 4 taken along line 5-5.

Referring to FIGS. 3-5, a wedge 100 is shown for maintaining reduction in a reduced distal radius fracture 15 or otherwise fixating adjacent bone. The wedge 100 has a longitudinal axis L and includes a body 110 and an anchorage reinforcement member 140, as described hereinafter, for maintaining reduction of a reduced fracture. In some instances, the wedge 100 is manufactured from a hard, non-compliant material such as stainless steel, titanium, other metal, non-metallic, or specialized medical grade polymer configured to conform to a fractured site of interest. The wedge 100 is preferably fabricated by additive manufacturing techniques, e.g., by any one or any combination of fused deposition modeling (FDM), selective laser sintering (SLS), selective laser melting (SLM), electron beam melting (EBM), and other appropriate 3D printing technologies known to those of skill in the art, including fabrication processes disclosed in U.S. Pat. Nos. 7,537,664; 8,728,387; 9,180,010; and 9,456,901, the disclosures of which are hereby incorporated by reference in their entireties herein as if fully set forth herein.

In a preferred embodiment, the body 110 is generally wedge-shaped and extends along the longitudinal axis L from a proximal end wall 112 to a distal end wall 114. However, the body 110 may be any suitable shape, in addition to a wedge, such as conical, a rectangular prism, or U-shaped, to the extent that the body 110 provides support to bone, alone or in combination with the anchorage reinforcement member 140 as described hereinafter.

The body 110 may include a tapered first, or top, surface 116 and a tapered second, or bottom, surface 118. The top surface 116 extends from an upper end 120 of the proximal end wall 112 to the distal end wall 114 and tapers toward the longitudinal axis L in the proximal to distal direction while the tapered bottom surface 118 extends from a lower end 122 of the proximal end wall 112 to the distal end wall 114 and tapers toward the longitudinal axis L in the proximal to distal direction. Thus, the proximal end wall 112 has a greater height than the distal end wall 114 such that as the wedge 100 is implanted into the metaphyseal void (shaded area of FIGS. 1 and 2) the tapered top and bottom surfaces 116, 118 force apart and stabilize the diaphysis 20 and the epiphysis 22 portions of the radius 10. More particularly, the tapered top and bottom surfaces 116, 118 prevent the diaphysis 20 from collapsing toward the epiphysis 22 and also provide lateral support to prevent lateral shifting and/or pivoting of the diaphysis 20 and the epiphysis 22 relative to one another.

With particular reference to FIG. 3, the top surface 116 and the bottom surface 118 have mirrored inclinations such that an angle A1, formed between the proximal end wall 112 and the top surface 116, is equal in degree and mirrored with respect to the longitudinal axis L, relative to an angle A2, formed between the proximal end wall 112 and the bottom surface 118. However, it is contemplated that the tapered top surface 116 and the tapered bottom surface 118 could have dual (or different) inclinations. It is also contemplated that the size of the wedge 100 and the inclinations of the top and bottom surfaces 116, 118 could be modified based upon the size and shape of particular fractures or metaphyseal voids.

In the illustrated embodiment, an exterior portion of the top surface 116 and an exterior portion of the bottom surface 118 are flat and preferably smooth in order to facilitate insertion of the wedge 100 into the distal radius fracture 15. In this respect, the top and bottom surfaces 116, 118 of the body 110 slide against a surface of the diaphysis 20 adjacent the metaphyseal void and a surface of the epiphysis 22 adjacent the metaphyseal void while the anchorage reinforcement member 140 secures the wedge 100 in a desired position.

In other embodiments, not shown, the exterior portions of the top surface 116 and the bottom surface 118 may be roughened or include roughed areas to ensure immobilization and bone-ingrowth after implantation. Any bone growth-inducing surfaces as are known are contemplated.

The body 110 also includes lateral walls 124 extending from the proximal end wall 112 to the distal end wall 114. In the illustrated embodiment, the proximal end wall 112, the distal end wall 114, and the lateral walls 124 are perpendicularly positioned to the longitudinal axis L, however, in embodiments not shown, the proximal end wall 112, the distal end wall 114, and/or the lateral end walls 124 may be offset therefrom to accommodate different angles of implantation.

As illustrated in FIGS. 3 and 4, an aperture 126 is defined through the top surface 116 and the bottom surface 118, forming a cavity C within the body 110 for receiving the anchorage reinforcement member 140. A bore 128 may be defined through the proximal end wall 112 to provide a surgeon with access to the anchorage reinforcement member 140, as is described in more detail hereinafter.

In a preferred embodiment, the anchorage reinforcement member 140 is a screw and is rotatably secured within the cavity C of the body 110 and adapted to engage with the diaphysis 20 and the epiphysis 22 portions of the radius 10 to maintain reduction of the reduced bone fracture 15.

As shown in FIGS. 4 and 5, the screw 140, includes a screw body 142 and a self-tapping helical thread 144 extending radially outward therefrom. The screw body 142 is generally frustoconical in shape and rotatably received within the cavity C of the body 110 such that the screw body 142 extends along the longitudinal axis L.

The screw body 142 includes a head 146 provided at a proximal end 148 thereof. The head 146 may define a recess 150 for receiving an implantation device 180 (shown in FIGS. 8 and 9), for example, a hex key having a tip corresponding in shape to the recess 150. With particular reference to FIG. 3, the head 146 is aligned with the bore 128 defined in the proximal end wall 112 such that a surgeon can access the recess 150 via the bore 128. In the illustrated embodiment, the recess 150 is hexagonal in shape, however, it is understood that the recess can be any suitable shape, such as squared, crossed, triangular, octagonal, etc. corresponding to the tip of the implantation device 180.

The screw body 142 may include a tapered sidewall 152 defining a hollow reservoir R therein configured to hold bone graft material such as autograft or allograft for facilitating osteogenesis after implantation. In the illustrated embodiment, the sidewall 152 may extend from a circumferential edge 156 of the proximal end 148 to a distal end 154 and taper toward the longitudinal axis L in the proximal to distal direction. In certain embodiments, the taper of the sidewall 152 may correspond to the inclination of the top and bottom surfaces 116, 118 of the body 110.

A plurality of openings 158 may be formed between adjacent crests 160 of the helical self-tapping thread 144 for permitting bone growth from the bone graft material within the reservoir R. Bone growth is typically desired from within the reservoir R to areas outside the implant including the metaphyseal void. The bone growth material may be inserted into the reservoir R before the screw 140 is rotated into place and/or after it is fully or partially inserted.

While the device may be structured such that the bone graft material can dispel from the openings 158 during implantation, it is not necessary. Bone growth will ensue in any event. However, it may be desirable to fill the reservoir R with bone cement and ensure that the bone cement flows from the openings 158 either upon insertion or after implantation in which case the bone cement can be inserted and pressured into the reservoir R such that the bone cement is extruded out of the openings 158 for fixation. Likewise, polymers can be built into the reservoir R, and upon implantation a sonic melting technique is employed to melt the polymer and have it flow out of the openings 158 for fixation. Of course, the polymer can be inserted post-implantation either in a flowable, solid or other form after implantation. Here, U.S. Pat. Nos. 7,335,205; 9,226,784; and 9,724,206, each of which is incorporated herein by reference as if fully set forth herein, discloses ultrasonic welding technologies applicable herein.

As shown in FIG. 3, the self-tapping helical thread 144 extends through the aperture 126 defined in the top surface 116 and the bottom surface 118 of the body 110 such that the thread 144 contacts and taps into the radius 10 during implantation of the wedge 100. Accordingly, the self-tapping helical thread 144 secures the wedge 100 in the metaphyseal void preventing the wedge 100 from backing out (being proximally displaced from the metaphyseal void). The self-tapping helical thread 144 may be continuous or non-continuous and may be of uniform or varying pitch.

Figure 6:
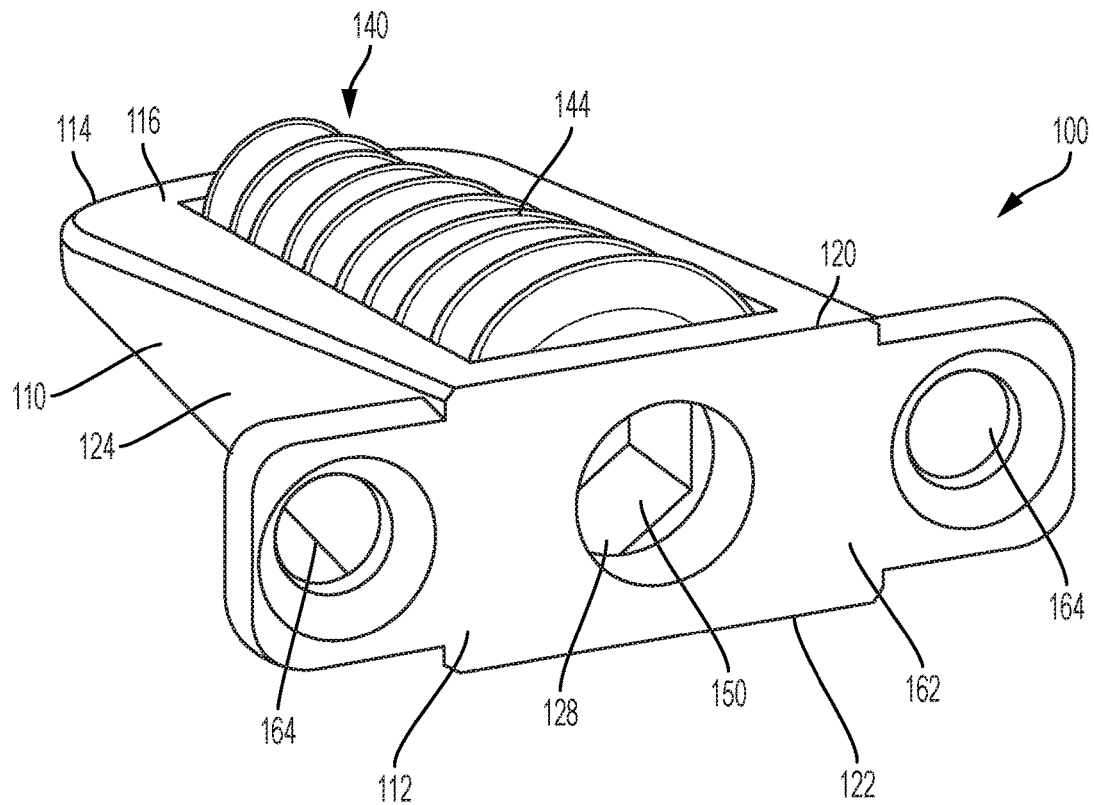
FIG. 6 is an isometric view of a wedge according to an embodiment of the invention.

Although, the screw 140 includes features that prevent the wedge 100 from backing out of the metaphyseal void, in one embodiment, as shown in FIG. 6, the wedge 100 may further include an attachment plate 162 provided at the proximal end wall 112 of the body 110 as an additional feature for preventing the wedge 100 from backing out of the metaphyseal void after implantation. The attachment plate 162 may be monolithically formed with the body 110 or manufactured as a separate and removable piece, attachable to the proximal end wall 112 of the wedge 100 before or after implantation of the wedge 100. The attachment plate 162 defines a pair of screw holes 164 through which screws (not shown) can be inserted to secure the attachment plate 162 to the radius 10 in order to further secure the wedge 100 and to prevent the same from backing out of the metaphyseal void.

In an alternative "push-in" type embodiment, the wedge body 110 is substantially the same as previously described, however, the wedge body 110 may be pushed or slide into the metaphyseal void simultaneously with, or separate from, the anchorage reinforcement member 140. Furthermore, the anchorage reinforcement member 140 may additionally or alternatively include a securement member such as teeth, barbs, protrusions, or similar securement member, as is known in that art, to anchor the anchorage reinforcement member 140, along with the attached body 110, to the radius 10 upon a translational and/or rotational movement.

In one embodiment, as is shown in FIGS. 7A-7D, the securement members may be provided on a single side, or opposing sides, of the sidewall 152' of the anchorage reinforcement member 140' such that the wedge 100 is transitionable between an unlocked position (FIGS. 7A and 7B), in which the securement members do not extend from the cavity of the wedge 100' and a locked position (FIGS. 7C and 7D), in which the securement members extend through the cavity of the wedge. While in the unlocked position (FIGS. 7A and 7B), a surgeon may simultaneously, or separately slide the wedge body 110' and the anchorage reinforcement member 140', into a desired position within the metaphyseal void and then rotate the anchorage reinforcement member 140' to a locked position, via a rotation of the anchorage reinforcement member, which may be any rotation including, for example, a 90° rotation, such that the securement member extends from the cavity and engages with the radius 10 to secure the wedge device 100' to the bone.

Figure 8:
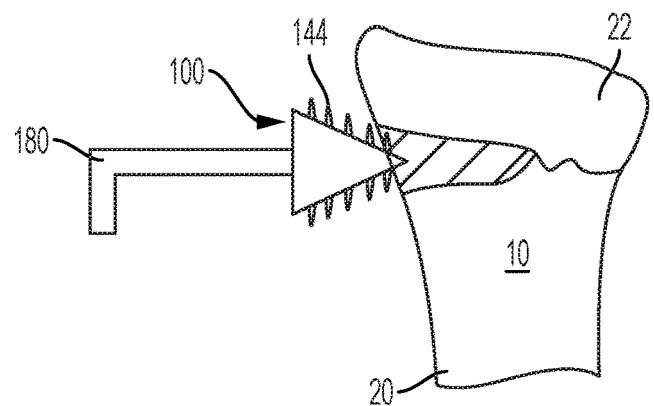
FIG. 8 is a side view of the wedge according to FIG. 3 during an initial step of implanting the wedge into the distal radius fracture.
Figure 9:
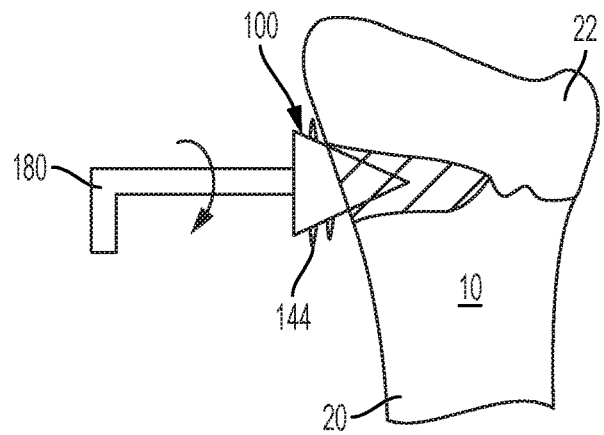
FIG. 9 is a side view of the wedge according to FIG. 3 intermediate the implantation of the wedge into the distal radius fracture.
Figure 10:
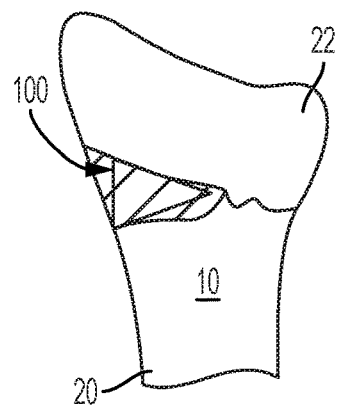
FIG. 10 is a side view of the wedge according to FIG. 3 after implantation of the wedge into the distal radius fracture has been completed.

FIGS. 8-10 illustrate a method of using the wedge 100 during osteotomy or to otherwise to maintain a reduced fracture. After a surgeon has reduced or properly aligned the radius 10, a distal end wall 114 is position within the metaphyseal void. As is shown in FIG. 8, depicting the onset of the implantation of the wedge 100, the epiphysis 22 has tilted downward toward the diaphysis 20.

In the embodiment, having the self-tapping screw 140, a tip of the implantation device 180 is then inserted through the bore 128 defined in the proximal end wall 112 of the body 110 and into the correspondingly shaped recess 150 defined in the head 146 of the screw. In order to drive the wedge 100 in place, the surgeon rotates the screw 140 clockwise relative to the body 110 which causes the self-tapping helical thread 144 to tap, or cut into, a surface of the diaphysis 20 adjacent the metaphyseal void and a surface of the epiphysis 22 adjacent the metaphyseal void.

While the securement members or helical thread 144 secure into the radius 10, the smooth exterior surface of the tapered top and bottom surface 116, 118 slides against a surface of the diaphysis 20 adjacent the metaphyseal void and a surface of the epiphysis 22 adjacent the metaphyseal void to facilitate wedging of the body 110 into the metaphyseal void, in the distal direction, as shown in FIGS. 9 and 10.

As the proximal end wall 112 of the body 110 wedges further into the metaphyseal void, the tapered top and bottom surfaces 116, 118 spread apart and sustain a separating force between the diaphysis 20 and epiphysis 22 portions of the radius 10. After the wedge 100 has been fully inserted into the metaphyseal void (FIG. 10), such that the proximal end wall 112 sits within the radius 10, the diaphysis 20 and epiphysis 22 portions of the radius 10 are returned to and secured in their proper alignment.

Alternatively, in the "push-in" type embodiment, while in the unlocked position, the surgeon pushes or wedges the body 100 in the distal direction such that the body 100 slides against a surface of the diaphysis 20 adjacent the metaphyseal void and a surface of the epiphysis 22 adjacent the metaphyseal void until the body 110 has been positioned at a desired location. Utilizing the implantation device 180 as previously described, the surgeon then rotates the anchorage reinforcement member 140 from the unlocked position (FIGS. 7A and 7B) to the locked position (FIGS. 7C and 7D), via a rotation of the anchorage reinforcement member 140, which may be any rotation including a 90° rotation, such that the securement members extend from the apertures 126 and engage with and secure the anchorage reinforcement member 140, along with the wedge body 110, to the radius or other bone.

The wedge 100 and method for using the same, described herein, simplify the maintenance of reducing a reduced fracture 15. More particularly, the tapered top and bottom surfaces 116, 118 prevent the diaphysis 20 and epiphysis 22 portions from collapsing toward each other and also prevent the diaphysis 20 and epiphysis 22 portions of the radius 10 from laterally shifting and/or pivoting relative to one another.

Advantageously, the self-tapping screw 144 of one embodiment secures the wedge 100 in place within the metaphyseal void thereby providing long-term stability to the wedge 100 until osteogenesis has occurred.

Nevertheless, in the embodiment disclosed in FIG. 6, after implantation and to provide additional stability to the device such that the wedge 100 is more securely prevented from backing out, the wedge 100 may optionally be further fastened to the radius 10 by securing screws (not shown) thorough screw holes 164 defined in the attachment plate 162 and into the radius 10.

Although the invention herein has been described with reference to particular embodiments, it is understood that the described embodiments are merely illustrative of the principles and applications of the present invention. It is therefore understood that numerous modifications may be made to the illustrative embodiments and that other arrangements may be devised without departing from the spirit and scope of the present invention as defined by the appended claims.

The invention claimed is:

1. A wedge for implantation into a distal radius fracture void, the wedge having a longitudinal axis and comprising:
   a wedge-shaped body extending along the longitudinal axis from a proximal end wall to a distal end wall and having flat opposing tapered surfaces tapering toward one another from the proximal end wall to the distal end wall, the wedge-shaped body having an aperture extending through the flat opposing tapered surfaces and defining a cavity within the wedge-shaped body; and
   a screw at least partially received within the cavity and being rotatable relative to the wedge-shaped body, the screw including a thread adapted to at least partially extend from the cavity to secure the wedge to bone.

2. The wedge of claim 1, wherein the thread is a self-tapping helical thread.

3. The wedge of claim 1, wherein the screw includes a shaft having a proximal end, a distal end and an outer diameter, and wherein the outer diameter of the shaft decreases from the proximal end of the shaft to the distal end of the shaft.

4. The wedge of claim 1, wherein a shaft of the screw defines a reservoir for receiving bone graft material.

5. The wedge of claim 4, wherein an outer surface of the shaft defines a plurality of openings.

6. The wedge of claim 1, wherein the screw includes a head having a hexagonal recess for receiving an implantation device.

7. The wedge of claim 6, wherein the implantation device is a hex key.

8. The wedge of claim 1, wherein the flat opposing tapered surfaces are adapted to slide against bone.

9. The wedge of claim 1, wherein the wedge-shaped body includes a roughened portion adapted to induce bone growth.

10. The wedge of claim 1, further comprising an attachment plate provided adjacent the proximal end wall, the attachment plate having at least one aperture for receiving a fastening member.

11. The wedge of claim 1, wherein the screw is rotatable a first position in which the thread is positioned entirely within the wedge-shaped body to a second position in which the thread at least partially extends out from the cavity.

12. The wedge of claim 11, wherein the thread is discontinuous and provided on opposing sides of the screw.

13. The wedge of claim 11, wherein a rotation of about 90 degrees moves the screw from the first position to the second position.

* * * * *